United States Patent [19]

Baugher

[11] 4,043,337
[45] Aug. 23, 1977

[54] DENTAL SYRINGE ATTACHMENT FOR SHOWER

[76] Inventor: Wilfred G. Baugher, 127 Yacht Haven Drive, Cocoa Beach, Fla. 32931

[21] Appl. No.: 704,314

[22] Filed: July 12, 1976

[51] Int. Cl.² ............................................. A61M 3/00
[52] U.S. Cl. ..................................... 128/229; 128/66
[58] Field of Search ................. 128/229, 66, 239, 230, 128/231

[56] References Cited

U.S. PATENT DOCUMENTS

| 3,499,440 | 3/1970 | Gibbs | 128/66 |
| 3,500,824 | 3/1970 | Gilbert | 128/66 |
| 3,593,707 | 7/1971 | Pifer | 128/66 |
| 3,682,176 | 8/1972 | Kelsen | 128/229 |
| 3,820,532 | 6/1974 | Eberhardt et al. | 128/66 |
| 3,870,045 | 3/1975 | Vaughan | 128/229 |
| 3,973,558 | 8/1976 | Stouffer et al. | 128/66 |

Primary Examiner—John D. Yasko
Attorney, Agent, or Firm—Duckworth, Hobby, Orman, Allen & Pettis

[57] ABSTRACT

This invention relates to a dental syringe for coupling between a water outlet and shower head. An adapter having a main passageway therein is furnished for coupling between the water outlet and the shower head for passing water therebetween. A main diverter valve is coaxially within a main passageway through the adapter for coupling the water under pressure to the shower head when the main diverter valve is in a first position, and diverting the water under pressure to the dental syringe when the diverter valve is in a second position. The dental syringe is coupled to a flexible conduit which is in turn coupled to the shower head adapter. The dental syringe includes a secondary control valve axially rotatable within a syringe passageway for controlling the volume of water expelled from the outlet port of the syringe. A combination holder and shield is coupled to the flexible conduit for storing the dental syringe therein.

14 Claims, 7 Drawing Figures

DENTAL SYRINGE ATTACHMENT FOR SHOWER

BACKGROUND OF THE INVENTION

1. Field of the Invention

This invention related in general to dental hygiene syringes and in particular to a dental syringe coupled to a shower head for obtaining water under pressure therefrom.

2. Description of the Prior Art

Recent research in dental hygiene indicates that improper brushing and excessive use of toothpastes which have floride or whitening additives may actually irritate and damage the gums. These studies suggest that perhaps the long accepted practice of using bristled toothbrushes for cleaning the teeth could be replaced with a more modern and hygentically efficient method. Dentists have recognized the limitations in the brushing method and have long ago adopted hydraulic irrigators for office use in cleaning teeth and messaging the gums.

Recent consumer products have adopted this dental irrigation technique for everyday use in cleaning teeth. However, many of these devices available to the consumer utilize a pulsating pressure for propelling the water against the teeth. Many people complain that the pulsations can irritate the gums and actually make the gums sore after prolonged use. Also, the pulsations exacerbate the splattering problems encountered when the front teeth are cleaned. Another problem common to most dental irrigators is the accumulation and discharge of the fluid propelled from the dental syringe. Normally the user is required to bend over a sink, or other similar recepticle, and to periodically expel the fluid from the mouth. This process, together with the aforementioned method of cleaning the front teeth, can and often do lead to a splattering of water or cleaning fluid about the general area.

One solution to these problems would be to utilize the shower area for cleaning the teeth. This would allow the user to concentrate on carefully and completely cleaning the teeth rather than concentrating on preventing the splattering of water about the general area.

Several inventor's have concentrated upon combining a dental irrigator with an adaptor for coupling to a bathroom water faucet, such as the type used in combination with a wash bowl. Inventions of this type are disclosed by Pinkston in U.S. Pat. No. 3,227,380; Harper in U.S. Pat. No. 3,386,439; and Gilbert in U.S. Pat. No. 3,467,082. A similar device is disclosed by Hyser in U.S. Pat. No. 2,550,565, which passes the irrigating water over a chemical compound for being used to clean the teeth. Blankfield in U.S. Pat. No. 2,855,930, discloses the use of a dental irrigator permanently attached, both physically and hydraulically, to a water faucet.

Matterson in U.S. Pat. No. 2,829,645 discloses a valve and dental hygene syringe for coupling to both the hot and cold water system to allow the controlled release of water of a selectable temperature. Powers in U.S. Pat. No. 3,465,751, discloses the use of dental irrigator in combination with a motor driven toothbrush.

Van Linge in U.S. Pat. No. 3,461,870, discloses the use of a douche attachment for connected with a shower. The attaching mechanism utilizes a cylindrical control element inserted transversely through the passageway for coupling water from the source to the shower head.

SUMMARY OF THE INVENTION

This invention relates to a dental syringe for coupling between a water outlet and a shower head. The dental syringe apparatus includes adaptor means having a main passageway therein for being coupled between the water outlet and the shower head for passing water therebetween. The main passageway includes a main valve cavity therein having a longitudinal axis generally parallel with a longitudinal axis of the main passageway. The adaptor means further includes a diverter passageway exiting the adaptor means from within the main valve cavity. The dental syringe apparatus further includes a main diverter valve coaxially coupled within the main valve cavity within the adaptor means. The main diverter valve includes a primary passageway axially therethrough for coupling with the main passageway for conducting water therethrough when the main diverter valve is in a first position. The main diverter valve further includes a by-pass passageway for coupling with the water outlet end of the main passageway and the by-pass passageway for conducting water therethrough when the main diverter valve is in a second position. Conduit means are coupled to the adaptor means at the diverter passageway for receiving the water under pressure therefrom. A manual syringe handle couples with the conduit means for receiving the water under pressure therefrom, with the manual syringe handle having a syringe passageway axially therein and an outlet port for receiving the water under pressure and for forming a water jet.

In a first preferred embodiment of the present invention, the manual syringe handle includes a secondary valve cavity having a longitudinal axis parallel with a syringe passageway. A secondary control valve rotates within the secondary valve cavity for controlling the flow of water under pressure therethrough to the outlet port.

BRIEF DESCRIPTION OF THE DRAWINGS

Other objects, features and advantages of this invention will be apparent from a study of the written description and the drawings in which.

DETAILED DESCRIPTION OF THE PREFERRED EMBODIMENT

Figure 1:
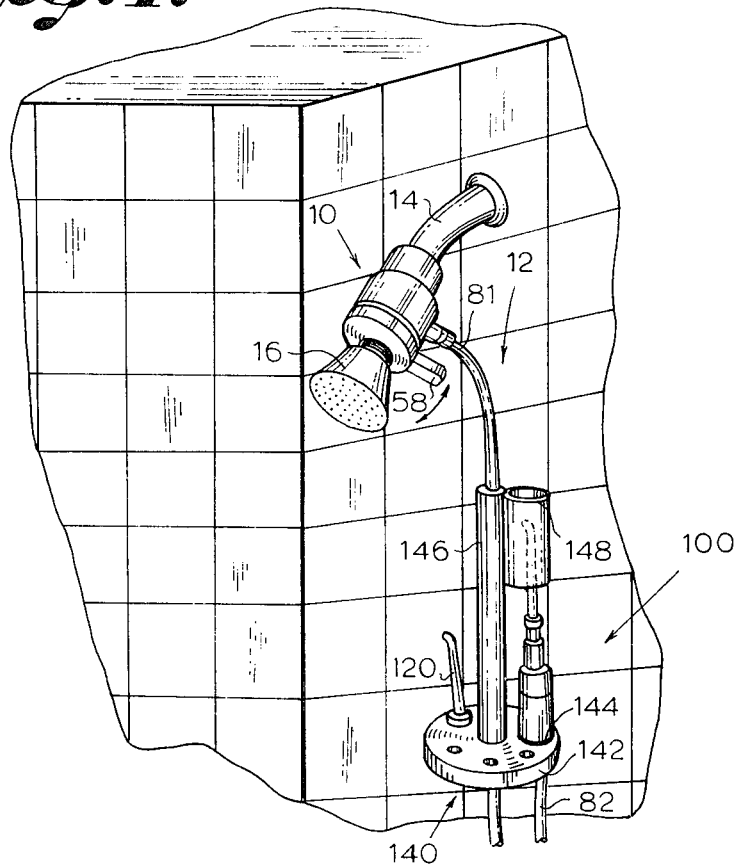
FIG. 1 is a frontal perspective view of the dental syringe apparatus coupled to a shower head.

A first preferred embodiment of the dental syringe attachment for a shower is illustrated generally in FIG. 1. The apparatus includes an adaptor, shown generally as 10, including a main diverter valve therein which coupled a shower head to the source of water under pressure. A conduit having a manual syringe handle coupled thereto, both shown generally as 12, is coupled to the main diverter valve.

Figure 2:
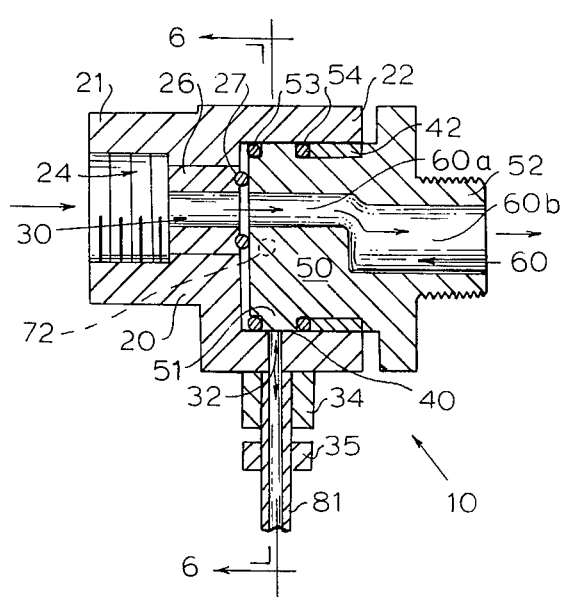
FIG. 2 is a side cross-section view of the main diverter valve in the first position for coupling water therethrough to the shower head.
Figure 3:
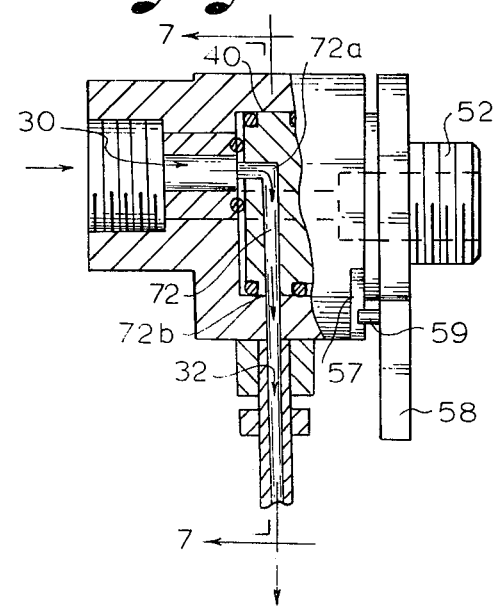
FIG. 3 is a side cross-section view illustrating the main diverter valve in the second position for coupling water to the dental syringe.
Figure 5:
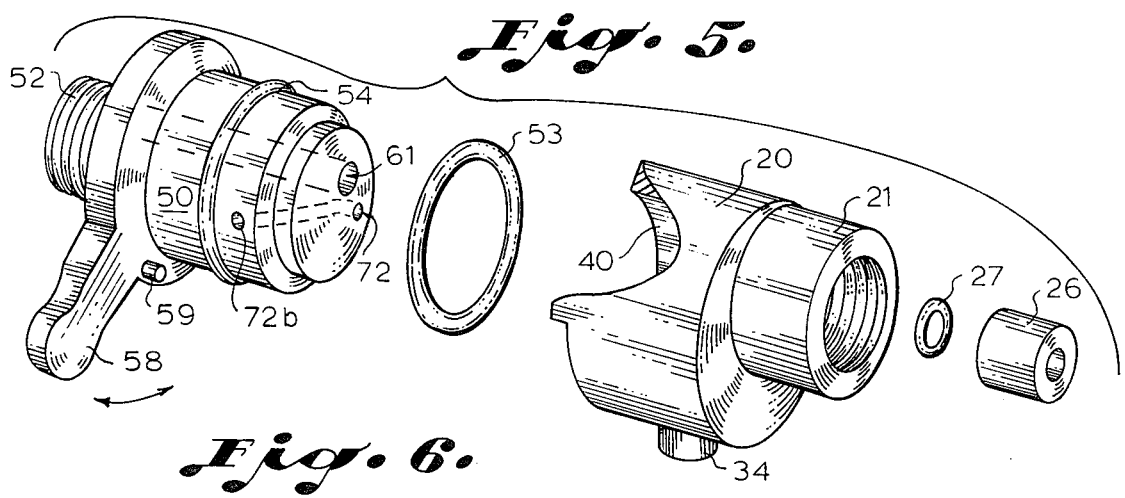
FIG. 5 is an exploded perspective view of the main diverter valve.

As illustrated in FIGS. 2, 3 and 5, the adaptor assembly 10 includes a generally cylindrically valve body 20 having a smaller diameter first end 21 for coupling with the source of water under pressure and a larger diameter second end 22. The smaller diameter first end 21 includes a threaded cavity 24 therein for coupling with a threaded section of a shower pipe 14 as illustrated in FIG. 1. The larger diameter second end 22 includes coaxially therein a main valve cavity 40 having a longitudinal diameter generally parallel to but offset from the longitudinal diameter of the threaded coupling cavity 24. An intermediate cavity is defined internal to the valve body 20 between the threaded coupling cavity 24 and the main valve cavity 40. A generally cylindrical sealing plug 26 is inserted within the intermediate cavity. A generally cylindrical main passageway 30 is coaxially located within the sealing plug 26 for coupling the threaded coupling cavity 24 to the main valve cavity 40. A first O-ring seal 27 is recessed into a planar surface of the sealing plug 26 adjacent the main valve cavity 40. A generally cylindrical diverter passageway 32 communicates from within the main valve cavity 40, passes through the valve body 20 and into a coupler 34.

A main diverter valve, shown generally as 50, is coaxially coupled within the main valve cavity 40 of the valve body 20. A larger diameter annular head section 51 includes a planar surface for abutting the first O-ring seal 27 in the sealing plug 26. The annular head section 51 further includes a second O-ring seal 53 and a third O-ring seal 54 recessed about the outer circumference thereof for producing a fluid tight seal against the inside diameter of the main valve cavity 40. A central section of the main diverter valve 50 communicates through a generally open-end of the main valve cavity 40 defined by a generally annular coupling lip 42 which is designed to couple with the third O-ring seal 54 to restrain the movement of the head section 51 within the main valve cavity 40. A second end 52 of the main diverter valve 50 extends outside of the main valve cavity 40 and includes thereon a plurality of threads for coupling with the shower head 16.

Figure 6:
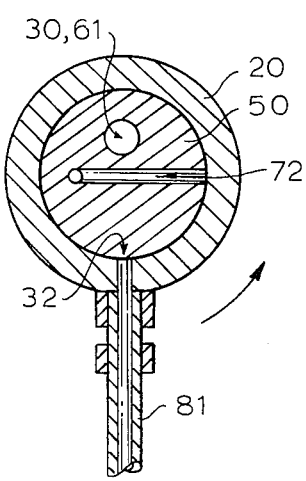
FIG. 6 is a cross-sectional view taken along section lines 6—6 in FIG. 2.

As illustrated in FIGS. 2 and 6, a primary passageway 60 comprises a generally cylindrical multi-sectioned bore communicating through the main diverter valve 50 from a point adjacent the main passageway 30, to feed water under pressure into the shower head 16 attached to the second end 52 of the main diverter valve 50. The first end 60a of the primary passageway couples with the main passageway 30 and is generally offset from a central longitudinal axis of the main diverter valve 50. The first section 60a of the primary passageway couples with a second end 60b thereof which is generally coaxial within the second end 52 of the main diverter valve 50. In this manner, when the main diverter valve 50 is in a first position, the main passageway 30 will couple directly into the primary passageway 60 for allowing water under pressure to pass therethrough into the shower head 16.

Figure 7:
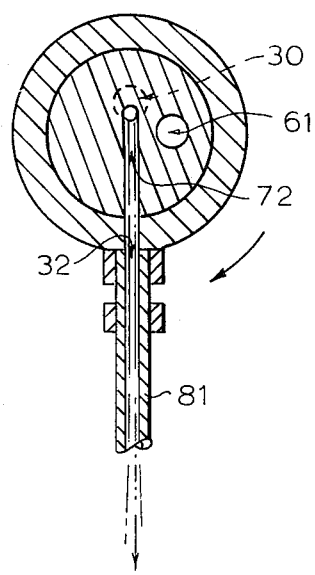
FIG. 7 is a cross-sectional view of the main diverter valve taken along section lines 7—7 as shown in FIG. 3.

As illustrated in FIGS. 3 and 7, a by-pass passageway is also contained within the annular head section 51 of them main diverter valve 50. When the main diverter valve 50 is rotated into a second position, a first end 72a of the by-pass passageway 72 will couple directly with the main passageway 30. A second end 72b of the by-pass passageway 72 will couple directly with the diverter passageway 32 in the outer circumference of the main diverter valve 50.. In this manner, when the main diverter valve 50 is retated to the second position, the water under pressure will travel through the main passageway 30, through the by-pass passageway 72 and into the diverter passageway 32. A handle section 58 is coupled to the second end 52 of the diverter valve 50 for rotating the diverter valve 50 for rotating the diverting valve 50 by approximately 90°. As illustrated in FIGS. 6 and 7, the primary passageway 60 the by-pass passageway 72 are spaced apart by ninety degrees of angular rotation of the main diverter valve 50. A stop pin 59 is coupled to an inward facing section of the handle 58 for traveling within a channel 57 recessed within the valve body 20, thus for limiting the rotation of the main diverter valve 50 to the 90° angular rotation required to interchange the primary passageway 60 with the by-pass passageway 70.

Figure 4:
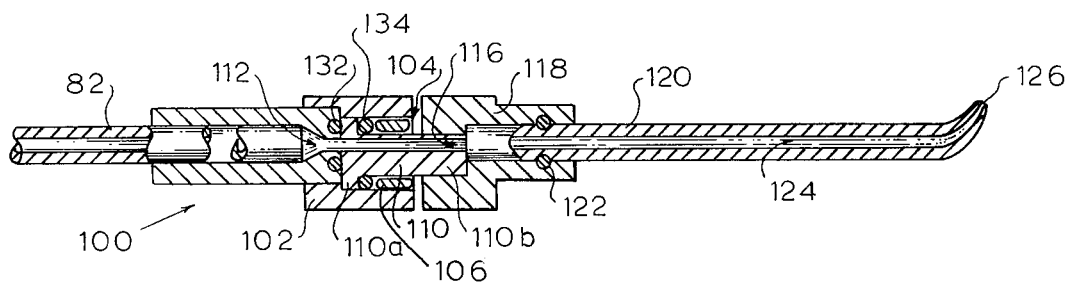
FIG. 4 is a side cross-section view of the manual syringe handle.

With reference to FIGS. 1 and 4, a first end 81 of a main conduit 80 (or tubing) is coupled to the coupling 34 by a threaded or snap-type attachment 35. The passageway within the main conduit 80 is thereby coupled directly with the diverter passageway 32 within the valve body 20. A second end 82 of the main conduit 80 is coupled to a manual syringe handle, illustrated generally as 100 in FIG. 4. The construction of the manual syringe handle 100 is generally similar to the construction of the adaptor assembly and main diverter valve 100. The manual syringe handle 100 includes generally cylindrical handle body 102 having a generally cylindrical secondary valve cavity 104 coaxially therein. An annular head section 110a of a secondary control valve 110 is restrained within the secondary valve cavity 104 by an annular lip section 106 depending from the handle body 102 into an open end of the secondary valve cavity 104. distended end 110b of the secondary control valve 110 extends from the open end of the secondary valve cavity 104 and couples coaxially to a syringe mounting section 118. A syringe tube 120 inserts within an aperture of the syringe mounting section 118 and is locked therein by a snap arrangement comprising an angular sealing ring 122 which rides within a generally annular groove within the internal aperture of the syringe mounting section 118 and an external annular groove on the syringe tube 120. In this manner, several different syringe tubes 120 may be alternately employed within the syringe mounting section 118. A syringe passageway 124 communicates through the syringe tube 120 to an outlet port 126 at the end thereof.

The secondary control valve 110 includes a control passageway 116 located therein parallel to, but offset from, the central axis of the generally secondary control valve 110. When the syringe mounting 118, to which the secondary control valve 110 is firmly attached, is rotated into a first position, the control passageway 116 within the secondary control valve 110 aligns with a syringe passageway 112 within the handle body 102 of the manual syringe handle 100. In this manner, the water transferred under pressure through the main conduit 80 will proceed through a syringe passageway section 112 within the handle body 102, then through the control passageway 116 in the secondary control valve 110, then into the syringe passageway 124 within the syringe tube 120, finally exiting in a water jet from the outlet port 126. The flow of water in the water jet from the outlet port 126 may be regulated by rotating the syringe mounting 118 and the secondary control valve 110 coupled thereto such that the control passageway 116 therein is not properly aligned with the syringe passageway 112 within the handle body 102. This rotation produces a misalignment between the two passageways because the control passageway 116, while axially located within the second control valve 110, is offset from the axis of rotation. Therefore, a rotation will displace the control passageway 116 into a second position in which it does not couple with the syringe passageway 112 in the handle body 102. Instead, a portion of the annular head section 110a of the secondary control valve 110 blocks the syringe passageway 112 within the handle body 102, thus preventing the passage of water therethrough. Two O-ring seals 132 and 134 are provided adjacent to the annular head section 110a of the secondary control valve 110 for eliminating water by-passing the annular head section 110a.

A combination holder and shield is shown generally as 140 in FIG. 1. The holder section comprises a disc 142 having a bore through the center thereof for slidably receiving therethrough a central section of the main conduit 80. The disc further includes a main storage slot 144 perpendicularly through the disc 142 and opening into the outer circumference thereof for allowing the second end 82 of the main conduit 80 to be inserted thereinto. The disc 142 also includes a plurality of bores spaced internal to the outer circumference thereof for receiving therein a plurality of syringe tubes 120.

A vertical tube 146 couples to the disc 142 adjacent the center aperture thereof and supports a generally cylindrically shield 148 immediately above the main storage slot 144. The cylindrical shield 148 includes therein a generally cylindrical cavity therein for receiving and covering the syringe tube 120 coupled to the handle body 102 of the manual syringe handle 100. In the manner, if water under pressure is accidentally applied to the annular syringe handle 100, the resulting water jet will be deflected within the cylindrical shield 148 so as not to startle or injure the unsuspecting occupant of the shower.

The operation of the dental syringe attachment will now be explained with reference to the FIGS. First, it will be assumed that the handle 58 is placed in the first position as shown in FIG. 6, for coupling water under pressure through the main passageway 30 and the primary passageway 60 into the shower head 16. In this manner the user may adjust the temperature and pressure of the water to suit his particular requirements. Next, the occupant of the shower grasps the manual syringe handle 100 and extracts the second end 82 of the main conduit 80 from the main storage slot 144. The operator then rotates the handle 58 into the second position as shown in FIG. 7, for moving the primary passageway 60 out of communication with the main passageway 30, and moving the by-pass passageway 72 into communication with the main passageway 30 for routing the water under pressure therethrough and into the diverter passageway 32. This water under pressure is then coupled through the main conduit 80 into the manual syringe handle 100. The operator may then rotate the syringe mounting 118 for adjusting the alignment of the control passageway 116 with the syringe passageway 112 within the handle body 102, thereby further regulating or controlling the pressure of the water as it exits the output port 126 in a water jet. Once the temperature and pressure of the water jet has been controlled for the comfort of the operator, the syringe tube 120 may be inserted into the mouth of the occupant of the shower for cleaning the teeth and between the gums in the normal manner.

The preferred embodiment of the dental syringe attachment for a shower has been described as an example of the invention as claimed. However, the present invention should not be limited in its application to the details illustrated in the accompanying drawings and the specification, since this invention may be practiced or constructed in a variety of other different embodiments. Also, it must be understood that the terminology and descriptions described herein are used solely for the purpose of describing the general operation of the preferred embodiment and therefore should not be construed as limitations on the operability of the invention.

I claim:

1. A dental syringe for coupling between a water outlet and a shower head, said apparatus comprising in combination:

adapter means having a main passageway therein for being coupled between the water outlet and the shower head for passing water therebetween;

a main diverter valve interposed along said adapter means for passing water therethrough when in a first position, and for diverting the water into a diverter passageway within said adapter means when said main diverter valve is in a second position, said main diverter valve having a first cylinder coaxially rotatable within a main valve cavity interposed along said main passageway, and said first cylinder having an axis of rotation generally parallel with but offset from said main passageway, with said first cylinder including therein a primary passageway for coupling the water under pressure therethrough when in said first position, and with said first cylinder further including a by-pass passageway therein for coupling the water under pressure from said main passageway to said diverter passageway when said first cylinder is in said second position;

conduit means having a first end coupled to said adaptor means at said diverter passageway for receiving water under pressure therefrom;

a manual syringe handle for coupling to a second end of said conduit means for passing water under pressure therefrom through a syringe passageway and an outlet port therein for forming a water jet; and a secondary control valve interposed along said syringe passageway of said manual syringe handle for passing water therethrough when in a first position, for blocking the flow of water therethrough when in a second position, and for variably restricting the flow of water therethrough between said first and second positions, said secondary control valve having a second cylinder coaxially rotatable within a second valve cavity interposed along said syringe passageway, with said second cylinder having an axis of rotation generally parallel with but offset from said syringe passageway, said second cylinder including therein a control passageway for coupling with said syringe passageway when said second cylinder is in said first position, whereby said second cylinder blocks the flow of water therethrough when rotated into said second position.

2. A dental syringe for coupling between a water outlet and a shower head, said apparatus comprising in combination:

adapter means having a main passageway therein for being coupled between the water outlet and the shower head for passing water under pressure therebetween, with said main passageway including therein a main valve cavity having a longitudinal axis generally parallel with a longitudinal axis of said main passageway, with said adapter means further including a diverter passageway exiting said adapter means from said main valve cavity therein;

a main diverter valve coaxially coupled within said main valve cavity of said adapter means, said main diverter valve including a primary passageway therein for coupling with said main passageway for conducting water therethrough when said main diverter valve is in a first position, with said main diverter valve further including a by-pass passageway therein for coupling the water under pressure from said main outlet passageway into said by-pass passageway when said main diverter valve is in a second position;

conduit means coupled to said adapter means at said diverter passageway for receiving the water under pressure therefrom; and a manual syringe handle for coupling with said conduit means for receiving water under pressure therefrom, said manual syringe handle having a syringe passageway therein and outlet port coupled thereto for receiving the water under pressure and forming a water jet and further having a secondary valve cavity interposed along said syringe passageway of said manual syringe handle, with said secondary valve cavity having a longitudinal axis generally parallel with a longitudinal axis of said syringe passageway and a secondary control valve coaxially coupled within said secondary valve cavity and having axially therethrough a control passageway for coupling with said syringe passageway when said second control valve is in said first position, whereby said secondary control valve blocks said syringe passageway when in said second position.

3. The dental syringe as described in claim 2 wherein said main diverter valve is a cylinder having said primary passageway passing axially therethrough for communicating with said main passageway of said adapter means.

4. The dental syringe as described in claim 3 wherein said by-pass passageway communicates through said diverter valve from an input side of said main passageway to a point on a circumferential surface thereof opening into said diverter passageway when in said second position.

5. The dental syringe as described in claim 3 wherein a section of said diverter valve extends through a generally open output end of said main valve cavity.

6. The dental syringe as described in claim 5 wherein said adapter means includes an annular lip projecting radially into said generally open output end of said main valve cavity for restraining an annular head of said main diverter valve therein.

7. The dental syringe as described in claim 6 wherein said extending section of said main diverter valve includes threaded coupling means thereon for coupling with the shower head.

8. The dental syringe as described in claim 7 wherein said extending section of said main diverter valve includes primary handle means coupled thereto for rotating said main diverter valve between said first and second positions.

9. A dental syringe as described in claim 3 wherein said secondary valve cavity is generally cylindrical and includes a generally open end defined by an annular rim depending from said manual syringe handle and wherein a central section of said secondary control valve extends outwardly through said open end of said secondary valve cavity, with an annular head section of said secondary control valve being restrained within said secondary valve cavity by said annular rim of said manual syringe handle.

10. A dental syringe as described in claim 9 wherein said manual syringe handle further comprises in combination:

a syringe tube having said syringe passageway axially therein and said outlet port at a distended end thereof; and syringe tube coupling means for removably coupling a second end of said syringe tube and said syringe passageway therein to said central section of said secondary control valve and said control passageway therein, whereby separate syringe tubes may be detachable coupled to said manual syringe handle.

11. A dental syringe as described in claim 10 wherein said syringe tube coupling means is a snap coupler comprising an annular groove within said control passageway for congruently coupling such an annular ring seated in an external surface of said syringe tube.

12. A dental syringe as described in claim 3 further comprising a combination:

holding means coupled to a section of said conduit means for removably receiving therein said manual syringe handle; and shield means spaced from said holding means for receiving said outlet port therein when manual syringe handle is stored within said holding means.

13. A dental syringe as described in claim 12 wherein said holding means comprises a frame having an aperture located therein for receiving said conduit means therethrough, said from further including a main storage slot for removably receiving said manual syringe handle therein and further including therein a plurality of said syringe tubes herein.

14. A dental syringe as described in claim 16 wherein said shield means comprises:

a hollow cylinder having a first closed end and a second open end for receiving therein set outlet port of said syringe tube when said manual syringe handle is stored within said holding means; and tube support means coaxially coupled to said conduit means and said frame for supporint said hollow cylinder vertically above said main storage slot.

* * * * *